United States Patent [19]
Saul et al.

[11] Patent Number: 5,618,735
[45] Date of Patent: Apr. 8, 1997

[54] FLUORESCENT LIPID POLYMER-MACROMOLECULAR LIGAND COMPOSITIONS

[75] Inventors: Tom Saul, El Granada; Georges Der-Balian; Paul Kenney, both of Mountain View; Heidi Mathis, Burlingame; Shirley Johnson, Mountain View; Hans Ribi, Hillsborough; Tom Witty, Santa Cruz, all of Calif.

[73] Assignee: Biocircuits Corporation, Sunnyvale, Calif.

[21] Appl. No.: 405,549

[22] Filed: Mar. 16, 1995

Related U.S. Application Data

[62] Division of Ser. No. 89,975, Jul. 9, 1993, Pat. No. 5,415,999.

[51] Int. Cl.$^6$ ............... G01N 33/53; G01N 33/543
[52] U.S. Cl. ............... 436/518; 422/57; 422/60; 435/7.9; 435/7.91; 435/7.92; 435/7.94; 435/968; 436/805
[58] Field of Search ............... 435/7.9, 7.91, 435/7.92, 7.94, 968; 436/518, 805; 422/57, 60

[56] References Cited

U.S. PATENT DOCUMENTS

| | | | |
|---|---|---|---|
| 4,193,983 | 3/1980 | Ullman et al. | 424/12 |
| 4,489,133 | 12/1984 | Kornberg | 428/408 |
| 5,268,305 | 12/1993 | Ribi et al. | 436/501 |

OTHER PUBLICATIONS

Lochner et al., Photoconduction in Polydiacetylene Multilayer Structures and Single Crystals, Phys. Stat. Solidi, 88:653–661. 1978.

Miller et al., Antibody Properties for Chemically Reversible Biosensor Applications, Analytica Chimica Acta, 224:135–143. 1989.

O'Shannessy et al., Specific Conjugation Reactions of the Oligosaccharide Moieties of Immunoglobulins, Journal of Applied Biochemistry. 7:347–355. 1985.

Owen, V.M., Non-electrode Biosensors in Clinical Biochemistry, Ann. Clin. Biochem. 22:559–564. 1985.

Sugi M., Langmuir-Blodgett Film – A Course Towards Molecular Electronics: A Review, Journal of Molecular Electronics. 1:3–17. 1985.

Thompson et al., Biosensors and Bioprobes, Trends in Analytical Chemistry, 3:7:173–178. 1984.

Wilson et al., Polydiacetylene Monolayers Functionalized with Amino Acids, Langmuir. 8:2361–2364. 1992.

Primary Examiner—Christopher L. Chin
Assistant Examiner—Bao-Thuy L. Nguyen
Attorney, Agent, or Firm—Flehr Hohbach Test Albritton & Herbert LLP

[57] ABSTRACT

Methods and compositions are provided for the detection of analytes. The method employs a fluorescence production layer which comprises a fluorescent polymerized polyunsaturated lipid layer in association with a ligand which is a member of a specific binding pair, where the ligand is competitive with the analyte for the complementary binding member or is a complementary binding member. By providing for a fluorescence modulation reagent which binds to the fluorescence production layer in proportion to the amount of analyte in the sample, by measuring the resulting fluorescence after carrying out the assay methodology, the amount of analyte can be determined quantitatively.

12 Claims, No Drawings

FLUORESCENT LIPID POLYMER-MACROMOLECULAR LIGAND COMPOSITIONS

This application is a division of application Ser. No. 08/089,975, filed on Jul. 9, 1993, now U.S. Pat. No. 5,415,999.

TECHNICAL FIELD

The field of this invention is the detection of molecules by means of fluorescent materials in association with materials capable of binding to a substance to form a specific binding pair.

BACKGROUND

As the world has become more complex and as our understanding of different phenomena has increased, there has been a concomitant need to improve methods of measuring the wide variety of substances. From the clinical laboratory, there has been increasing interest in being able to measure various substances in the doctor's office, the home, at bedside, in the field, as well as other sites. With the continuously increasing number of physiologically active substances, both naturally occurring and synthetic, there has been a desire to be able to measure these substances as indicative of the health status of an individual, for therapeutic dosage monitoring, for research, and the like. The substances may be found in a wide variety of samples, ranging over numerous orders of magnitude in concentration for their dynamic ranges of activity, and further differ as to the ease with which one may detect their presence. An area which has only recently assumed substantial commercial importance and will be of increasing importance is the detection of specific nucleotide sequences. Nucleotide sequences find application in genetic counseling, forensic medicine, detection of diseases, and the like. There is, therefore, a wide diversity of opportunities to measure diverse substances from different sources with different sensitivities and for a wide range of purposes.

The methods for detection have ranged from radioactive labels, light absorption, fluorescence, chemiluminescence, agglutination, etc. Each of these methods has found application and has disadvantages as well as advantages over alternative methods. As yet, there has been no single method which has proven applicable in all situations. There is, therefore, substantial interest in devising new methods which may provide for significant opportunities in measuring compounds of interest, where the protocols, apparatus, or reagents may provide advantages over other techniques.

RELEVANT LITERATURE

U.S. Pat. No. 4,489, 133 describes procedures and compositions involving orderly arrays of protein molecules bound to surfactants. Thomas, et al., *Electron. Letters* (1984) 20:83–84 describe a GaAs/LB film MISS switching device employing ω-tricosenoic acid as the surfactant bilayer for producing a thin insulator. Lochner, et al., *Phys. Status Solidi* (1978) 88:653–661 describe photoconduction in polydiacetylene multilayer structures and single crystals. Sugi, *J. Molecular Electronics* (1985) 1:3–17 provides a review of Langmuir-Blodgett film use in electronics. Reynolds, ibid (1986) 2:1–21 describes conducting organic polymers. Wilson, *Electron. Letters* (1983) 19:237 describes the principles of a three dimensional molecular electronic memory employing polydiacetylene crystals or Langmuir-Blodgett multilayer films. Descriptions of electronic devices employing organized macromolecular ensembles formed with surfactant layer crystallization include Arrhenius, et al., *Proc. Natl. Acad. Sci. USA* (1986) 83:5355–5359; Haddon and Lamola, Ibid (1985) 82:1874–1878; and Paleos, *Chem. Soc. Rev.* (1985) 14:45–67. Vandevyer, et al., *J. Chem. Phys.* (1987) 87:6754–6763. U.S. Pat. No. 4,624,761. Fujiki, et al., *Amer. Chem. Society* (1988) 4:320–326. Biegajski, et al., *Amer. Chem Society* (1988) 4:689–693. Pecherz, et al., *Journal of Molecular Electronics* (1987) 3:129–133. Lando, et al., *Synthetic Metals* (1984) 9:317–327. Day, et al., *Journal of Applied Polymer Science* (1981) 26:1605–1612. Shutt, et al., *Amer. Chem. Society* (1987) 3:460–467. Dhindsa, et al., *Thin Solid Films* (1988) 165:L97–L100. Metzger, et al., *Amer. Chem. Society* (1988) 4:298–304. Fujiki, et al., *Amer. Chem. Society* (1988) 4:320–326. Wohltjen, et al., *IEEE Transactions on Electron Devices* (1985) 32:1170–1174. Wernet, et al., *Semiconducting L-B Films* (1984) 5:157–164. Sugi, et al., *Thin Solid Films* (1987) 152:305:326. Peterson, *Journal of Molecular Electronics* (1986) 2:95–99. Descriptions of methods for immobilizing biological macromolecules on polymerized surfactant films include: O'Shannessey, et al., *J. Appl. Bioch.* (1985) 7:347–355. Hashida, *J. Appl. Biochem.* (1984) 6:56–63. Packard, et al., *Biochem.* (1986) 25:3548–3552. Laguzza, et al., *J. Med. Chem.* (1989) 32:548–555. Jimbo, et al., *Journal of Molecular Electronics* (1988) 4:111–118. Hanifeld, *Science* (1987) 236:450–453. Goundalkar, *Communications* (1984) 36:465–466. Cress, et al., *Amer. Biotec. Lab.* (February 1989) 16–20. Biosensors employing surfactant layer crystallization are described by Owen, *Ann. Clin. Biochem.* (1985) 22:555–564 and Thompson and Krull, *Trends in Anal. Chem.* (1984) 3(7):173–178. Bader, et al., *Advances in Polymer Sci.* (1985) 64:1–62 describe polymeric monolayers in liposomes as models for biomembranes.

Miller and Anderson, *Anal. Chim. Acta.*, (1989) 227:135–143, described a fiber-optic sensor based on a homogeneous fluorescence energy-transfer immunoassay and the chemical kinetics.

SUMMARY OF THE INVENTION

Sensors are provided comprising a fluorescent layer in conjunction with non-covalently bound specific binding pair members, where the fluorescent layer of particular interest is a conjugated polyunsaturated lipid extended chain. The fluorescent layer is employed in association with macromolecular ligands which are conveniently non-covalently associated with the fluorescent layer. Assays are performed, where a reagent is employed which modulates the fluorescent properties of the fluorescent layer. By employing either competitive or sandwich assays, the modulation of the fluorescence may be related to the amount of analyte in a sample. By employing a fluorimeter, the fluorescence may be measured and related to the amount of analyte.

DESCRIPTION OF THE SPECIFIC EMBODIMENTS

Methods and compositions are provided employing a sensor for the detection of analytes. Central to the methods and compositions is a fluorescent layer, particularly a monolayer comprising polymerized lipids, polymerized through double and triple bonds to form an extended polyunsaturated chain which is fluorescent and whose fluorescence may be modulated by appropriate reagents.

The polymerized polyunsaturated lipid layer can serve as a transducer for amplifying a signal resulting from an assay component which affects the fluorescence of the layer. Thus, an agent which may serve as a chromophore, light absorber or scatterer, fluorophore or which agent has other properties which may affect the fluorescence can be measured more sensitively, by the amplification resulting from the interaction of such agent and the polymerized polyunsaturated lipid layer.

The capability of the polymerized polyunsaturated lipid layer may be exemplified by using the polymerized polyunsaturated lipid layer on a support and bringing the polymerized lipid layer in proximity to a fluorescence modulation reagent capable of influencing the fluorescence of the lipid layer, either directly or indirectly, and measuring the fluorescence of the lipid layer as compared to a known amount of fluorescence modulation reagent in proximity to the polymerized polyunsaturated lipid layer, including the substantial absence of the fluorescence modulation reagent. The fluorescence modulation reagent will be non-covalently associated with the polymerized polyunsaturated lipid layer in sufficient proximity so as to affect the response of the polymerized polyunsaturated lipid layer to light irradiation. By relating the amount of the fluorescence modulation reagent in proximity to the polymerized polyunsaturated lipid layer to an analyte of interest, the fluorescence observed can be quantitatively related to the amount of analyte in a sample. The polymerized lipid layer can be physically separated from the analyte being assayed such that the binding event leads to the production of an effector which modulates the lipid layer's fluorescence.

For assays, in addition to the polymerized lipid layer are macromolecular ligands which can compete with an analyte for binding to a reagent (competitive mode) or bind to the analyte so as to bind the analyte in association with the fluorescent layer (sandwich mode), where the analyte may then act as a bridge to bind the moiety. (The combination of polymerized polyunsaturated lipid layer and macromolecular ligand will be referred to as the "fluorescence production layer.") The macromolecular ligand has at least one binding site of interest. The fluorescence modulation reagent may be one or more molecules and includes a specific moiety that can interact with the polymerized polyunsaturated lipid layer when in proximity to the polymerized polyunsaturated lipid layer and which serves to modulate the fluorescence of the polymerized polyunsaturated lipid layer, usually resulting in a reduction in fluorescence in proportion to the amount of analyte in a sample.

In carrying out the assays, a sample, which may have been subjected to pre-treatment, is added to the fluorescence production layer and incubated for sufficient time for binding to occur, where the fluorescence modulating reagent may be present or absent. Where the assay is a competition assay in that the ligand present in the fluorescence production layer competes with analyte in the sample for the fluorescence modulation reagent, the sample may be combined concomitantly with the fluorescence modulation reagent and the fluorescence production layer or have been combined with the fluorescence modulation reagent prior to addition to the fluorescence production layer. Where the assay is a sandwich assay, in that the analyte serves as a bridge between the fluorescence production layer and the fluorescence modulation reagent, then the sample and fluorescence modulation reagent may be added concurrently or consecutively in any order. After incubation for sufficient time for binding to occur, as appropriate, additional reagents may be added, followed by a determination of the fluorescence of the fluorescence production layer.

For the formation of lipid films, a temperature gradient technique may be employed (see U.S. application Ser. Nos. 366,651, filed Jun. 15, 1989 and 453,784, filed Dec. 20, 1989). Surfactant, including amphophiles, films may be formed on the surface of an aqueous subphase by standard lipid monolayer technologies. A solution containing a monomeric surfactant composition, dissolved in an organic solvent, is applied to the subphase surface by a micropipet. Solvents may include hydrocarbons such as pentane, hexane, heptane, and decane or chlorocarbons such as mono-, di-, tri- or tetrachloroethane. The subphase may be composed of pure water, glycerol, polyethylene glycol, or other polar organic solvents miscible with water.

Monomeric polymerizable surfactants are spread on the subphase at a concentration ranging from 0.01 to 50 milligrams/milliliter of spreading solvent. The aqueous medium may be pre-heated to disperse the surfactant usually to a temperature of not more than about 130° C., which results in evaporation of the solvent. The medium is then allowed to cool to below room temperature, usually to below about 20° C. The rate of cooling may by regulated by the traverse rate of the subphase slide from the heating element to the cooling element, where typical traverse rates vary from 1 cm/second to 1 cm/minute. When the subphase temperature is raised above the surfactant melting temperature, the non-polymerized regions of film will become fluid. When the subphase is cooled back below the surfactant melting transition, crystals of monomers nucleate from the crystalline polymer region.

The surfactant is then polymerized employing any convenient initiation system, e.g., ultra-violet light. The rate of polymerization will be related to the light intensity, so that shorter times will be employed with higher intensity irradiation. Polymerization times between 0.1 seconds to 3 minutes are generally satisfactory.

The film quality can be inspected optically using methods such as polarization birefringence, lateral diffusion techniques including lateral film pressure, or fluorescence measurements such as fluorescence recovery after photobleaching. Films are inspected for defects, crystal domain size and shape, and integrity. The film may be transferred to different substrates for production of the sensor. Transfer is typically accomplished by slowly lowering a transfer substrate planar to the surfactant film at the air/subphase interface. Contact is made at one end of the subphase surface and then full transfer is accomplished by decreasing the contact angle to zero. Transfer may also be achieved by applying standard Langmuir-Blodgett methods [George L. Gaines Jr.: Insoluble Monolayers at Liquid Gas Interfaces, Interscience Publishers, I. Prigogine Editor, John Wiley and Sons (1964)].

The polymerizable surfactants have been extensively described in the literature as evidenced by the prior art described previously. The composition of the surfactant layer may be homogeneous where the surfactant is polymerizable and has a polar terminus, or heterogeneous, where a mixture of surfactants are employed, some of which are polymerizable and others which are not polymerizable.

The surfactant molecule may have a single lipid chain, e.g., a diynoic acid or a plurality of lipid chains, e.g., diester glycerides, preferably a single chain, and generally not more than two lipid chains. Of particular interest are diynoic amides of dihydroxyamine, particularly of from about 20 to 30 carbon atoms, more particularly of from about 22 to 26 carbon atoms.

Illustrative surfactants include N-(1,2-dihydroxy-3-propyl) pentacosa-10,12-diynamide, ethanolamino-10,12-pentacosadiynamide, 6,8-hexadecadiynoic acid, 2-hydroxyethyl octadeca-8-10-diynoate, eicosa-12,14-diynyl-10, 12-phosphatidyl serine, pentaeicosa-10,12-diynoic acid, tricosa-10, 12-diynoic acid, acetylene compounds with multiple diyne groups and other polymer surfactants including single acyl chain polymerizable surfactants.

Various other surfactants may be present as diluents for the polymerizable surfactant. These surfactants may be naturally occurring, synthetic, or combinations thereof, and may be illustrated by laurate, stearate, arachidonate, cholesterol, bile acids, gangliosides, sphingomyelins, cerebrosides, or the like.

Various functional groups may be present in the film to provide for polymerization, which allow for Förster energy transfer. For the most part, the functional groups will comprise diynes, although other unsaturated molecules may find use, such as activated diynes, e.g., α-ketodiynes.

For the most part, the hydrophobic portion of the surfactant will have a chain of at least 6 aliphatic carbon atoms, usually a straight chain of at least 6 aliphatic carbon atoms, and generally not more than a total of about 100 carbon atoms, usually not more than about 34 carbon atoms. Preferably, the number of carbon atoms in the hydrophobic portion of the chain will vary from about 12 to 32, more usually 20 to 30, and more preferably 23 to 28 carbon atoms.

The lipid molecules will terminate in a hydrophilic moiety, cationic, anionic or neutral (nonionic) where the functionalities may include non-oxo carbonyl, e.g., carboxylic acids, esters and amides, oxo-carbonyl, such as diols, aldehydes or ketones, oxy, such as ethers, polyethers, and hydroxyl, amino, such as primary, secondary, and tertiary amines and ammonium, phosphorus acids esters and amide, such as phosphate, phosphonate, and phosphonamide, sulfur functionalities, such as thiol, sulfonates, sulfate, and sulfonamides, and the like. Usually, the polymerizable functionality will be separated from the polar and non-polar termini by at least one carbon atom, generally from about 1 to 50 carbon atoms, more usually from about 1 to 8 carbon atoms. The polymerizable group is typically incorporated into the hydrophobic interior of the surfactant film. Diacetylenic groups are typically incorporated in the hydrocarbon chain of the surfactant so that more than one group is present for polymerization. By having two or more polymerizable groups in the surfactant chain, a multiplicity of electrically conducting and/or optically active polymers may be obtained. This configuration leads to films of higher structural integrity and mechanical strength.

Variations of the headgroup provide for improved film quality, such as stability of the film, surface charge, control of inter-head-group hydrogen bonding, reduction of non-specific binding or fluid matrix effects, and ease of chemical modifications. The hydrocarbon tail of the surfactant may also terminate in a hydrophilic group so that the surfactant is bipolar. [Sher, *Justus Liebigs Ann. Chem.* (1954) 589:234; and Akimoto, et al. *Angew. Chem.* (1981) 20(1):91)].

The macromolecular ligand which is non-covalently associated with the lipid layer to form the fluorescent production layer, can be any convenient molecule, which is greater than 5 kD, usually at least about 10 kD molecular weight, more usually at least about 15 kD, and will generally be not more than about 1000 kD, more usually not more than about 500 kD. The ligand is characterized by being a member of a specific binding pair which is able to compete with the analyte for the complementary member of the specific binding pair or is able to bind to the analyte, where the analyte is the complementary binding member. Where the analyte is a macromolecule, the analyte may serve as the ligand for association with the lipid layer. Where the analyte molecular weight is below about 10 kD, particularly below about 5 kD, e.g. a hapten, the haptenic analyte or molecule having competitive binding characteristics, will be bound, usually covalently bound, to a macromolecule of at least about 10 kD, frequently, 15 kD or more. The number of haptenic molecules bound will be at least 1, usually at least 2, generally not more than about 1 per 5 kD, more usually not more than about 1 per 10 kD. Manners of conjugating a wide variety of analytes of interest are extensively described in the literature, the particular manner in which ligands are bound to the macromolecular molecule is not critical to this invention.

For the most part, the macromolecular ligand will be a polymer, conveniently a protein, although other polymeric molecules may be employed, both naturally-occurring or synthetic. Various polymeric compositions include nucleic acids, polysaccharides, hyaluronic acids, polysiloxanes, polyacrylates, etc. The macromolecular ligand will either bind to the lipid layer, the solid support supporting the lipid layer, or both, so as to provide a stable association during the course of the use of the lipid layer.

The manner in which the fluorescence production layer is formed can be varied widely, where the two components can be combined by any convenient means, which provides for retention of the macromolecular ligand in association with the lipid layer. For example, the macromolecular ligand may be coated onto a solid support, where it becomes bound, either covalently or non-covalently, and the lipid layer deposited over the macromolecular layer. Various substrates can be employed to which the macromolecular ligand will bind, including glass, plastic, or the like. Of particular interest is the use of proteins as the macromolecular ligand, in conjunction with various plastics, e.g. polystyrene, polypropylene, polyethylene, polyolefin copolymers, polycarbonate, methacrylates, PMPP, SAM, and the like, where the protein will strongly adhere to the plastic surface and the solid support is compatible with the assay reagents, conditions and the polymerized polyunsaturated lipid layer. Instead of having the macromolecular ligand bound to the substrate initially, the lipid layer may first be applied and adhered to the substrate, followed by addition of the macromolecular ligand in an appropriate liquid medium to the lipid layer. In either event, the macromolecular ligand becomes bound to the substrate and/or fluorescent layer, usually the substrate, since the lipid layer will allow the macromolecular ligand to contact the substrate.

In many instances, the macromolecular ligand may be a receptor molecule, which binds to the analyte. A wide variety of receptor molecules are available, which primarily include antibodies or binding fragments thereof, e.g. Fab, $F(ab')_2$, or the like, enzymes, lectins, and for the purposes of this invention, nucleic acids. Thus, these receptors may serve to bind the analyte, which will be the complementary member of the specific binding pair.

The amount of macromolecular ligand will generally be coated on about 0.01 to 100%, more usually 1 to 10% of the solid surface. So long as there lo is a sufficient amount of the macromolecular ligand to ensure that the amount of macromolecular ligand will not be limiting in measuring the amount of analyte.

The macromolecular ligand may be applied to the substrate in an appropriate buffered medium, generally at pH in the range from about 2–10, more usually about 5–9. The concentration of macromolecular ligand in the medium will generally be at least about 0.01 μg/ml and not more than about 100 μg/ml, more usually being from about 0.10–5 μg/ml, where the amount of macromolecular ligand may be substantially in excess of the amount that can be absorbed by the substrate. The amount of macromolecular ligand which is bound to the substrate will vary depending upon the manner of application, the nature of the macromolecular ligand and analyte, the dynamic range of the analyte, the fluorescent modulating reagent, and the like.

The manner of coating may be dipping, spraying, brushing, rolling, or the like. The surface to be coated, preferably uncontaminated, will be completely exposed to the medium and incubated for sufficient time, generally less than about 1 min to ensure that there is substantially complete coating of at least a portion of the substrate surface. Since the opposite surface will not be exposed to the assay medium, where the solid support is a slide, the slide may be submerged in the medium. Generally, the temperature will be in the range of about 1–50° C., more usually about 10–40° C. After the surface has been exposed for sufficient time for binding to occur, the surface may be removed from the macromolecular ligand containing medium, washed with water, particularly distilled water or deionized water, and then allowed to dry or used directly for the lipid film transfer. Where the lipid film transfer occurs prior to the macromolecular ligand binding, the solid support with the lipid film may be treated in substantially the same way as described above for binding of the macromolecular ligand.

The fluorescent lipid films can be formed at the gas-liquid interface and then transferred to the solid support. Transfer can be readily achieved by using conventional Langmuir-Blodgett conditions. The thickness of the solid support supporting the lipid layer will generally be from about 5–100 mil. The solid support provides the desired structural support. Depending upon the nature of the solid support, it may be desirable to modify the solid support surface to provide for the binding of the macromolecular ligand and lipid film to the surface. Desirably, for glass, the surface may be silanized in accordance with conventional ways. For plastic, chemically reactive groups may be used to functionalize the surface, e.g. chloroakyl, iminohalide, acyl, amino, formyl, etc.

Once the fluorescence production layer is formed on the solid support, it may then be used for detection of an analyte.

In assays, the fluorescence modulation reagent will include a binding member of the specific binding pair, which member either competes with the analyte for binding to the macromolecular ligand or binds to the analyte bound to the macromolecular ligand. The specific binding member may be conjugated to a quencher chromophore, where the absorption of the quencher overlaps the emission band of the fluorescence of the polymerized polyunsaturated lipid layer or, preferably, to an enzyme which produces a product which can affect the fluorescence of the lipid layer, particularly quenching the fluorescence.

Quenching can be achieved in a number of ways. The most straight-forward way is to have a product which is a dye which absorbs the fluorescence emission light. Thus, where the dye absorbs the emission light, particularly where it is deposited on the lipid layer, there will be a substantial reduction in fluorescence. Alternatively, the product may be a fluorescer which has an absorption band which overlaps the emission band of the polymerized polyunsaturated lipid layer. In this manner, by reading fluorescence in the emission band of the lipid layer, particularly at or about the wavelength range of the peak emission, a reduction in emission intensity, as compared to the absence of the product will provide a measure of the amount of analyte. Alternatively, one may read the fluorescence of the product by measuring the emitted light at or about the emission maximum of the product, where the intensity of emission will be related to the amount of analyte in the sample.

A wide variety of enzymes may be employed in the conjugate. Of particular interest are hydrolases, which allow for production of a fluorescent product or an absorptive dye from a leuco dye. There are many chromophores which may be functionalized as ethers or esters, where the chromophoric properties are substantially different from the unfunctionalized compound. Of particular interest are phenolic compounds which have strong absorptive properties as the free phenol, but are weakly or non-absorptive in the absorption band of the free phenol when functionalized. Thus, one can prepare galactosidyl ethers and use β-galactosidase, phosphate esters and use alkaline phosphatase, sulfate esters and use sulfatases, sialic acid derivatives and use neuraminidase, etc. Various quenchers of interest include fluorescein, umbelliferone, phycobiliprotein, etc, The manner of conjugation is not critical to this invention, there being numerous illustrations in the literature of conjugation of compounds to enzymes. Where the analyte is a protein, by employing recombinant technology, one may provide for fused proteins comprising the analyte and the enzyme or enzyme subunit. Otherwise, various known linking groups may be employed which allow for covalent binding of the analyte to the enzyme, e.g. glutaraldehyde, maleimidobenzenesulfonate or carboxylate ester, Ellman's reagent, etc. For fluorescent molecules, various known linking groups may be employed for linking the fluorescer to the analyte. Thus, depending upon the nature of the analyte, the particular linkage will vary widely. In conjugating the analyte to the fluorescer or enzyme, it is important that the conjugate be able to bind to the analyte and, as appropriate, the macromolecular ligand.

In carrying out the assay, the sample, used directly or subject to pre-treatment, may be applied to the fluorescence production layer. Various pre-treatments may be involved, such as removal of cells, extraction, dilution, lo heating, addition of a variety of releasing reagents, or the like. For the most part, the samples will be physiological samples, such as blood, urine, cerebro-spinal fluid, saliva, milk, and the like. However, in many other situations, the samples may be derived from process stream effluents, water, air, soil, or other environmental material, animal tissue, human tissue, and the like. In some instances, the analyte of interest may involve particles, such as virus particles, cells, organelles, microsomes, and the like. The significant factor is that the analyte can be dispersed substantially homogeneously and be maintained dispersed in the assay medium during the period of the assay or may be spread over the surface of the fluorescence production layer and non-specific components removed by washing.

The fluorescence modulation reagent may be combined with the sample and other components of the assay medium, e.g. buffer, prior to contact with the fluorescence reduction layer or subsequent to the contact of the assay medium with the fluorescence production layer. In some instances, the fluorescence modulation reagent may be combined with the fluorescence production layer prior to the addition of sample. Of particular interest is where the fluorescence production layer is combined with the sample under conditions, usually anhydrous conditions, where the fluorescence modulation reagent will not react with the fluorescence production layer. By addition of sample, the fluorescence modulation reagent becomes dissolved and may then react in the assay medium as appropriate. In this manner, measurement of the amount of fluorescence modulation reagent to be added may be avoided.

The amount of fluorescence modulation reagent will vary, depending upon whether the assay is a competitive assay or sandwich assay. In the case of the competitive assay, the amount of reagent will vary depending upon the concentration range of interest of the analyte. It may vary from about 0.1, more usually 0.5 times the lowest concentration in the range of interest of analyte to not more than about 10 times, usually not more than about 5 times the highest concentration in the range of interest of the analyte. The particular amount chosen will depend upon a number of factors, such as the rate of binding of the reagent to analyte, the protocol employed, e.g. time of measurement, the range of interest, the sensitivity desired, and the like. In most instances, the particular concentration will be optimized as to a particular analyte.

After addition of the sample in the assay medium to the fluorescence production layer, in the absence of the fluorescence modulation reagent, the medium may be incubated for sufficient time to ensure complete binding. One may then wash to remove any non-specific binding materials present in the assay medium. Conveniently, the same or different buffer solution used for the assay medium may be employed for the washings. Usually, the washings will involve volumes not greater than 10 times, usually not greater than about 5 times the volume of the original assay medium. In the competitive mode, the washings may be followed by the addition of the fluorescence modulation reagent solution, conveniently in an appropriately buffered medium, and the system incubated for sufficient time for the fluorescence modulation reagent to bind to analyte bound to the fluorescence production layer. Non-specifically bound reagent may then be removed by washing. For the enzyme, this will be followed by the addition of substrate where a timed reaction will be performed. One can have a single-point determination, where the determination is made at a fixed time from the addition of the substrate to the enzyme conjugate, or can choose a rate of reaction, where the variation in fluorescence over a pre-determined timed interval may be used to determine the amount of conjugate bound to the fluorescence production layer.

Any analyte can be determined by the subject method. Ligands, such as haptens and antigens may be determined, where the ligands may include naturally-occurring or synthetic organic molecules, proteins, saccharides, nucleic acids, lipids, or combinations thereof. The ligands may be haptenic or antigenic, single molecules, polysubunit molecules, or aggregates, such as microsomes, cells, virus particles, or the like. The ligands may include various drugs, such as drugs of abuse, therapeutic drugs, toxins, or the like. The analytes may include surface membrane proteins, such as cluster designation proteins, HLA proteins, mutant proteins, lipopolysaccharides, peptide drugs, cancer markers, viral proteins, cyclodectrans, placental antigens, such as TSH, PTH, CEA, AFP, PJA, and PSA, ferritin, interferon, enzymes, cytoplasmic proteins, e.g. transcription factors, elongation factors, ribosomes, etc. Other ligands of interest may include hormones, such as thyroxine, triiodothyronine, growth hormone, steroids, vitamins, cofactors, etc.

Kits can be provided for use in the subject methodology, where the kits would comprise the polymerized polyunsaturated lipid layer on a solid support and the macromolecular ligand, conveniently in proximity to the layer and bound to the support. Also included would be the fluorescence modulation reagent, which may be the analyte or the complementary binding member bound to a fluorescent molecule or bound to an enzyme.

The following examples are offered by way illustration and not by way limitation.

EXPERIMENTAL

Example 1

Preparation of Thyroxine-Bovine Serum Albumin Conjugate (BSA-$T_4$)

A. L-thyroxine (5.0 g) was dispersed in 200 ml methanol, the solution saturated with gaseous HCl, allowed to stand overnight, at which time a precipitate formed. The supernatant was diluted with 400 ml diethyl ether, chilled and the precipitate isolated. The precipitate was then suspended in 10:1 methylene chloride/methanol, enough triethylamine added to make the solution clear on sonication, followed by passing the solution through a 50 mm×200 mm silica gel columne in 20:1 methylene/methanol and fractions containing the product isolated and stripped of solvent.

B. The $T_4$ methyl ester prepared above (8.3 g) was combined with 1.16 g triethylamine and 200 ml of chloroform and sonicated to dissolve the ester, followed by cooling in an ice bath. To the ester solution was added a solution of 1.28 g of diglycolic acid anhydrous in 300 ml of chloroform over about 1 h. After the solution was warmed to room temperature, it was stirred overnight. The reaction was monitored with TLC and upon completion, the solvent was stripped and the product passed through a 70 mm×200 mm silica gel column in 50:10:1 methylene chloride/methanol/acetic acid. Fractions containing the product were isolated, the solvent stripped and the precipitate washed with acetone.

C. Into 30 ml of DMF was added the $T_4$ diglycolic acid methyl ester (1.0 g) and N-hydroxy succinimide (NHS; 0.32 g), followed by 0.36 g of DCC. The solution was stirred overnight. The solution was then filtered and the filtrate used in the next step.

D. To 1.454 mg BSA in 145 ml of aqueous sodium bicarbonate with stirring was added the filtrate of C. over a time period of 0.5 h at a temperature of about 40° C. After stirring overnight at room temperature, the mixture was centrifuged for 1 h, the supernatatnt collected and dialyzed 4× for 1 h each time against 4 L of deionized water. The resulting solution having a concentration of about 6 mg/ml was diluted to 3 mg/ml with 2×PBS. Following, 1 ml of 10% $NaN_3$ was added to the diluted solution and the solution was refrigerated. The solution was warmed to room temperature prior to use.

Example 2

Preparation of Anti-$T_4$-Alkaline Phosphatase Conjugate

A. The alkaline phosphatase was dialyzed against 500 ml of alkaline phosphatase dialysis buffer (76.28 g sodium borate decahydrate in 3.75 ml $H_2O$) for 1.5 h with three changes of buffer at room temperature. The dialyzed solution was divided into 400 µl aliquots. 10 µl of 20 mg/ml sulfo-SMCC (sulfosuccinimidyl 4-[maleimidomethyl]) in DMF was added to each aliquot and the mixtures were incubated for about 45 min at room temperature. The reaction mixtures were then dialyzed overnight at 4° C. in modified alkaline phosphatase dialysate buffer (0.1 M Tris+ 5.0 mM $MgCl_2$+0.1 mM $ZnCl_2$, pH 7.0).

B. After dialyzing IgG-anti-$T_4$ (2.4 mg/ml) with mouse IgG dialysate buffer (50.0 mM phosphate +1.0 mM EDTA, pH 7.5), and bringing the volume to 1 ml with the dialysate buffer, 10 µl of SATA (N-Succinimidyl S-acetylthioacetate) solution, having a concentration of 1.3 mg SATA/ml DMF, was added and the reaction allowed to proceed for about 30 min at room temperature. The reaction product was dialyzed overnight at 4° C. against 500 ml of IgG dialysate buffer (50.0 mM phosphate +1.0 mM EDTA, pH 7.5).

C. After further dialysis of the modified alkaline phosphatase and the reduced anti-$T_4$-IgG, the modified alkaline phosphatase was split equally into two portions and combined with the two portions of reduced anti-$T_4$IgG, which has also been divided equally. The two resulting combinations were incubated for one hour at room temperature. 2 µl of NEM solution (0.1 g/ml N-ethylmaleimide in DMF) was added to each portion and the portions were further incubated for 30 min at room temperature. The portions were then combined in a 50 ml centrifuge tube and placed on ice. An equal volume of cold, saturated ammonium sulfate was added dropwise to the now combined portions. The resultant combination was then stirred in a refrigerator overnight.

The precipitate which formed was then centrifuged at 15,000×g for 30 min. The supernatant was discarded and the precipitate was resuspended in 450 µl of column equilibrium buffer (TBS+5.0 mM $MgCl_2$+0. 1 mM $ZnCl_2$ 0.1% $NaN_3$). The resuspended precipitate was then run through a column at a flow rate of 0.4 ml/min and aliquot numbers 21–31 (500 µl each) were retained and pooled. 10 mg of BSA were added to the pooled aliquots for every 1.0 ml of pooled aliquot.

Example 3

Preparation of the Polymerized Polyunsaturated Lipid Layer

The polymerized polyunsaturated lipid layer was produced as follows. First, a glass microscope slide was placed on a copper plate (10 cm×10 cm square and 0.4 cm thick). 2.0 ml of double glass distilled water was applied to one end of the glass slide. The temperature of the water subphase was 30° C. 2.0 µl of a solution of lipid monomers, for example N-(2',3'-dihydroxy)propyl-3 pentaeicosan-10,12-diynamide, was applied to the aqueous surface from a 5.0 µl micropipet at room temperature in two equal aliquots. Enough monomers were applied to achieve a surface area concentration of 1.7 mg/m². Upon evaporation of the solvent, the monomer dried into small visible islands at the water surface. The copper plate was transferred to a preheated hot plate (approximately 200° C. on the hot plate surface). The copper plate, the microscope slide, and the water were heated until the islands of monomer melted and dissolved at the water surface. The copper plate was transferred after 3–5 minutes heating to a prechilled aluminum block embedded in ice. The copper plate, slide and water were allowed to cool to 4° C.

The monolayer was then polymerized with a UV 254 nm short wave lamp (0.06 watts/cm²) at a distance of 2 in from the film for a period of 30 sec.

Example 4

Preparation of the Fluorescence Production Layer

A conjugate of thyroxine and bovine serum albumin was prepared as above, where the ratio of thyroxine to bovine serum albumin was in the range of 1:5 to 1:23. The BSA-$T_4$ was dissolved to a concentration of 33 mg/ml in Tris-buffered saline pH 7.6 at 25° C. After thorough mixing, an acrylic support was immersed in the buffer mixture and incubated for 1 h at 37° C. The acrylic support was then removed and thoroughly rinsed with distilled water.

The polymerized lipid film was then transferred to the support. Following, the film was treated with TBSt (Tris Buffered Saline containing 0.5% tween 20) by submerging the film, now associated with the solid support, in the TBSt solution and incubated for 10 min at room temperature.

Example 5

Assay of quantity of T4 in Blood Plasma

The fluorescence production layer was used to assay the amount of $T_4$ present in a given sample of plasma in the following manner. First, the fluorescence production layer was placed in contact with the serum sample. Next, a sufficient amount of ANS (8-anilino-1-napthalenesulphonic acid) was added to the sample so as to release the $T_4$ which was bound to thyroid binding protein. Addition of ANS resulted in the release of $T_4$ from the binding protein, resulting in free $T_4$ analyte. Following, the anti-$T_4$-alkaline phosphatase conjugate was added to the sample. The $T_4$ analyte and the bound BSA-$T_4$ both competed for binding to the conjugate. The amount of conjugate that bound to the BSA-$T_4$ was inversely proportional to the amount of $T_4$ analyte in the plasma. The remaining serum with the unbound $T_4$ analyte was washed away from the fluorescence production layer. The fluorescence of the film was then measured with a fluorimeter. Following, a solution of BCIP/NTC (5-bromo-4-chloro-3'-indolylphosphatem/neotetrazolium chloride) in Tris buffer was washed over the fluorescence production layer. The alkaline phosphatase, now bound to the BSA-$T_4$ of the fluorescence production layer, acted on the BCIP/NTC to release a dye. The dye quenched the fluorescence production layer and the new fluorescence was measured. By comparing the differences in the measured fluorescence readings with values from a standard curve, the amount of $T_4$ analyte in the serum sample was determined.

Example 6

Assay for $T_4$ in a Serum Sample Using Fluorescence Production Layer in Biocircuits I Instrument An assay cartridge, roughly the size of credit card, was formed for use in the Biocircuits I instrument. The top half of the cartridge comprised the fluorescence production layer as described above. The bottom half of the assay cartridge was separated into three areas. One area had ANS molecules adsorbed to it, a second had the alkaline-phosphatase conjugate (as prepared above) adsorbed to it, and a third had BCIP/NTC substrate adsorbed to it.

This cartridge was inserted into the Biocircuits I instrument and brought to 37° C. Following, 65 µl of serum, in which the concentration of $T_4$ was to be determined, was added to the sample port on the instrument. The plasma sample rehydrated the ANS on the cartridge. The rehydrated ANS released $T_4$ analyte from the thyroid binding proteins to which the $T_4$ had been bound in the serum. Next, the serum, which now comprised free $T_4$ analyte, rehydrated the portion of the cartridge with the anti-$T_4$-alkaline phosphatase adsorbed to it. $T_4$ analyte in the serum competed with the bound BSA-$T_4$ for binding to the rehydrated conjugate. The proportion of conjugate which bound to the BSA-$T_4$ was inversely proportional to the amount of $T_4$ analyte which was in the sample. Following sufficient time for competitive binding, the sample was washed away from the cartridge with 250 µl of Tris buffer (pH 9.5).

The fluorescence of the cartridge with bound conjugate was then measured. Following, 280 µl Tris buffer was washed over the cartridge so as to rehydrate the still dry BCIP/NTC substrate. Rehydration brought the substrate into direct contact with the alkaline phosphatase conjugate now bound to the BSA-$T_4$ on the cartridge. The alkaline phosphatase enzymatically released a blue dye from the rehydrated substrate which quenched the fluorescence of the fluorescence production layer. This enzymatic reaction was allowed to proceed for 10 min. The now quenched fluorescence was measured. By comparing the first fluorescence value with the quenched fluorescence value, the quantity of $T_4$ present in the original 65 µl sample was determined.

It is evident from the above results, that the subject methodology provides for a rapid and efficient assay for the determination of a wide variety of analytes. The detection system can be readily prepared, without requiring direct conjugation of the member of the specific binding pair to the lipid. In this manner, the assay is substantially simplified and the formation of the fluorescent lipid layer greatly simplified. A single component lipid film is more reproducible than currently existing two-component systems and the assay procedure is simplified in having fewer molecular building blocks.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A fluorescent layer comprising:
   (a) a solid support;
   (b) a macromolecular proteinaceous ligand adsorbed onto to said solid support; and
   (c) a polymerized polydiacetylene lipid layer layered onto said macromolecular proteinaceous ligand.

2. A fluorescent layer according to claim 1, wherein said solid support is a polymer plastic.

3. A fluorescent layer according to claim 2, wherein said plastic is a methacrylate.

4. A fluorescent layer according to claim 1, wherein said macromolecular proteinaceous ligand is an antigen.

5. A fluorescent layer according to claim 1, wherein said macromolecular proteinaceous ligand is a conjugate of a hapten bound to a protein.

6. A fluorescent layer according to claim 1, wherein said lipid layer comprises N-(2',3'-dihydroxy)propyl-3 pentaeicosano-10,12-diynamide.

7. A fluorescent layer comprising:
   (a) a solid support;
   (b) a macromolecular proteinaceous ligand covalently bound to said solid support; and
   (c) a polymerized polydiacetylene lipid layer layered onto said macromolecular proteinaceous ligand.

8. A fluorescent layer according to claim 7, wherein said solid support is a polymer plastic.

9. A fluorescent layer according to claim 8, wherein said plastic is a methacrylate.

10. A fluorescent layer according to claim 7, wherein said macromolecular proteinaceous ligand is an antigen.

11. A fluorescent layer according to claim 7, wherein said macromolecular proteinaceous ligand is a conjugate of a hapten bound to a protein.

12. A fluorescent layer according to claim 7, wherein said lipid layer comprises N-(2',3'-dihydroxy)propyl-3 pentaeicosan- 10,12-diynamide.

\* \* \* \* \*